United States Patent
Skarping et al.

(10) Patent No.: US 10,605,704 B2
(45) Date of Patent: Mar. 31, 2020

(54) METHOD FOR ACTIVE OR PASSIVE SAMPLING OF PARTICLES AND GAS PHASE ORGANIC AND NON-ORGANIC COMPONENTS IN A FLUID FLOW

(71) Applicant: PROVTAGAREN AB, Hässleholm (SE)

(72) Inventors: Gunnar Skarping, Hässleholm (SE); Marianne Dalene, Hässleholm (SE)

(73) Assignee: PROVTAGAREN AB, Hässleholm (SE)

(*) Notice: Subject to any disclaimer, the term of this patent is extended or adjusted under 35 U.S.C. 154(b) by 0 days.

(21) Appl. No.: 15/557,396

(22) PCT Filed: Mar. 11, 2016

(86) PCT No.: PCT/SE2016/050198
§ 371 (c)(1),
(2) Date: Sep. 11, 2017

(87) PCT Pub. No.: WO2016/144248
PCT Pub. Date: Sep. 15, 2016

(65) Prior Publication Data
US 2018/0113057 A1    Apr. 26, 2018

(30) Foreign Application Priority Data
Mar. 12, 2015  (SE) .................... 1550301

(51) Int. Cl.
*G01N 1/22*    (2006.01)
*G01N 1/10*    (2006.01)
(Continued)

(52) U.S. Cl.
CPC ............. *G01N 1/2247* (2013.01); *G01N 1/10* (2013.01); *G01N 1/2205* (2013.01);
(Continued)

(58) Field of Classification Search
CPC .......... G01N 1/22; G01N 30/02; G01N 35/00; G01N 1/2214; G01N 1/2205;
(Continued)

(56) References Cited

U.S. PATENT DOCUMENTS 5,254,861 A    10/1993  Carpenter et al.
5,302,191 A    4/1994   Koutrakis et al.
(Continued)

FOREIGN PATENT DOCUMENTS

EP    2275796 A1    1/2011
JP    53-071374 U   6/1978
(Continued)

OTHER PUBLICATIONS

Supplementary Partial European Search Report, completed on Feb. 26, 2019, from related European Application No. 16762064 filed on Mar. 11, 2016.
(Continued)

*Primary Examiner* — Brian J. Sines
(74) *Attorney, Agent, or Firm* — Preti Flaherty Beliveau & Pachios LLP

(57) ABSTRACT

A method for active or passive sampling of particles and gas phase organic and non-organic components in a fluid flow (4) is disclosed, wherein said method comprises the step in which a sampling device comprising a first denuder device (1), a filter device (3), and a second denuder device (2), arranged in axial direction in a series in said order, is provided at a measurement spot, wherein the first denuder device (1) and the second denuder device (2) each is hollow and contains surfaces provided with a hydrophobic and/or a hydrophilic sorbent, or said second denuder device (2) contains a packing of hydrophobic and/or hydrophilic sorbent particles, as well as a sampling device used in said method.

15 Claims, 4 Drawing Sheets

(51) Int. Cl.
*G01N 30/02* (2006.01)
*G01N 35/00* (2006.01)

(52) U.S. Cl.
CPC ......... *G01N 1/2208* (2013.01); *G01N 1/2214* (2013.01); *G01N 1/2273* (2013.01); *G01N 2001/1006* (2013.01); *G01N 2001/227* (2013.01); *G01N 2001/2223* (2013.01); *G01N 2001/2288* (2013.01)

(58) Field of Classification Search
CPC ......... G01N 2001/2223; G01N 1/2273; G01N 2001/1006; G01N 1/10
USPC .................... 436/43, 52, 139, 161, 177, 181
See application file for complete search history.

(56) References Cited

U.S. PATENT DOCUMENTS

| | | | |
|---|---|---|---|
| 5,763,360 | A | 6/1998 | Gundel et al. |
| 2005/0051719 | A1 | 3/2005 | Miller et al. |
| 2005/0133716 | A1 | 6/2005 | Miller et al. |
| 2009/0224150 | A1 | 9/2009 | Matyjaszczyk et al. |
| 2009/0317916 | A1 | 12/2009 | Ewing et al. |
| 2011/0203931 | A1 | 8/2011 | Novosselov et al. |
| 2012/0090411 | A1 | 4/2012 | Perlinger et al. |
| 2012/0329166 | A1* | 12/2012 | Skarping ................... G01F 1/68 436/106 |
| 2013/0192463 | A1 | 8/2013 | Wu et al. |
| 2015/0300225 | A1* | 10/2015 | Abdul-Khalek .......... F01N 3/02 95/90 |

FOREIGN PATENT DOCUMENTS

| | | | |
|---|---|---|---|
| JP | 5-157284 | A | 6/1993 |
| JP | 2003-294592 | A | 10/2003 |
| JP | 2005-241473 | A | 9/2005 |
| JP | 2006-214889 | A | 8/2006 |
| JP | 2006-215035 | A | 8/2006 |
| JP | 2009-047593 | A | 3/2009 |
| JP | 2010-259983 | A | 11/2010 |
| JP | 2013-521495 | A | 6/2013 |
| WO | 2000/14508 | A1 | 3/2000 |
| WO | 2000075622 | | 12/2000 |
| WO | 2004/104559 | A1 | 12/2004 |
| WO | 2007129965 | | 11/2007 |
| WO | 2009/091999 | A1 | 7/2009 |
| WO | 2009/092007 | A1 | 7/2009 |
| WO | 2009/092012 | A1 | 7/2009 |
| WO | 2011/055762 | A1 | 5/2011 |
| WO | 2011108981 | | 9/2011 |
| WO | 2013/132154 | A1 | 9/2013 |
| WO | 2013133872 | | 9/2013 |
| WO | 2014/045061 | A1 | 3/2014 |
| WO | 2014193302 | | 12/2014 |

OTHER PUBLICATIONS

Rowe, M. et al., Thermal extraction and analysis of atmospheric semivolatile organic compounds from multicapillary collection devices, Organohalogen Compounds, vol. 70, pp. 000038-000041; abstract (2008).

Geldenhuys, G., et al., Monitoring of atmospheric gaseous and particulate polycyclic aromatic hydrocarbons in South African platinum mines utilising portable denuder sampling with analysis by thermal desorption-comprehensive gas chromatography-mass spectrometry, Journal of Chromatography A, pp. 17-28; abstract; figure 1 (Feb. 2015).

Forbes, P., et al., The use of multi-channel silicon rubber traps as denuders for polycyclic aromatic hydrocarbons, Analytica Chimica Acta, 730, pp. 71-79; abstract; figure 1; (2012).

Gundel, L., et al., Direct determination of the phase distributions of semi-volatile polycyclic aromatic hydrocarbons using annular denuders, Atmospheric Environment, vol. 29, No. 14, pp. 1719-1733; abstract; figure 1 (1995).

Olson, D., et al., Sampling artifacts in measurement of elemental and organic carbon: Low-volume sampling in indoor and outdoor environments, Atmospheric Environment 39, pp. 5437-5445; abstract (2005).

International Search Report from International Application No. PCT/SE2016/050198, dated Jun. 14, 2016.

International Preliminary Report on Patentability from International Application No. PCT/SE2016/050198, dated Mar. 7, 2017.

Hinds, William C.: "Aerosol Technology" In: "Aerosol Technology: Properties, Behavior, and Measurement of Airborne Particles, 2nd Edition." New York: Wiley, 1999. Section 15.8: Electrostatic Precipitators, p. 338.

International Preliminary Report on Patentability, completed on Jun. 3, 2017, from related International Application No. PCT/SE2016/050159, filed on Nov. 3, 2016.

Supplementary European Search Report, completed on Oct. 19, 2018, from related National Phase Application No. EP 16762065, filed on Oct. 12, 2017.

\* cited by examiner

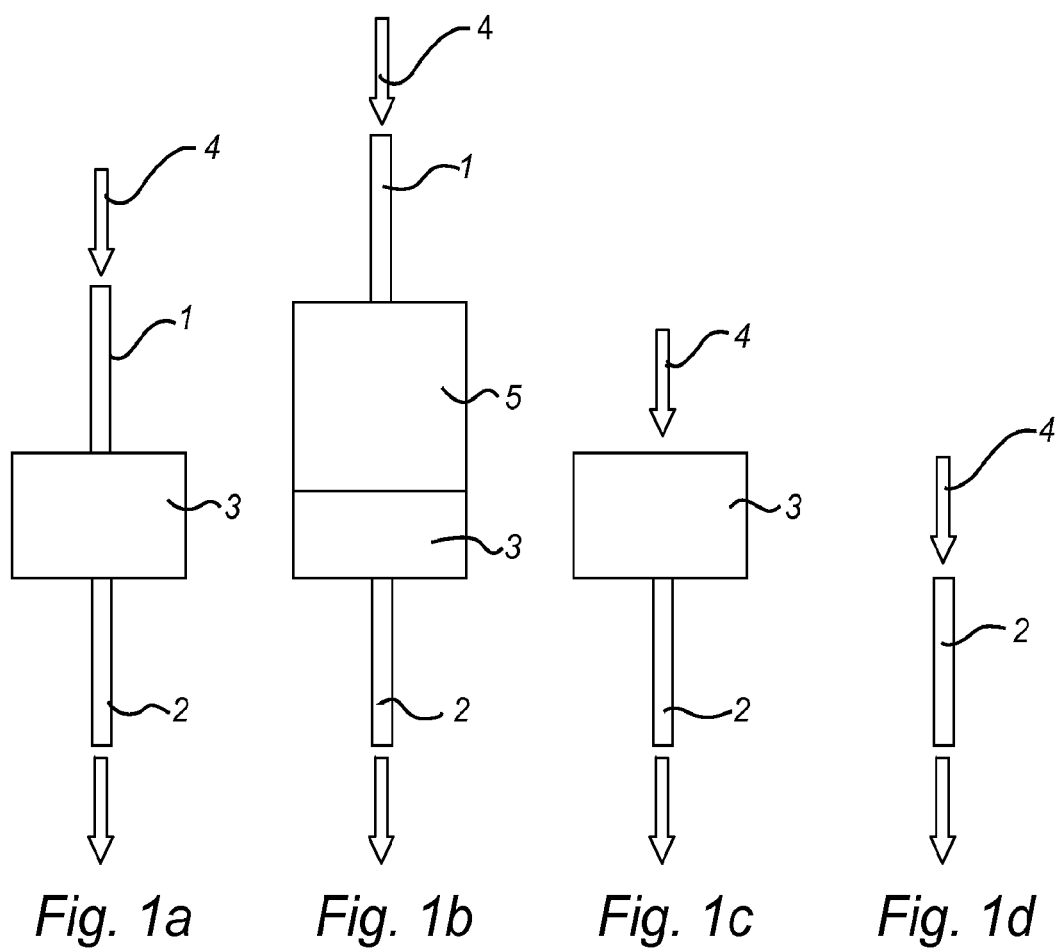

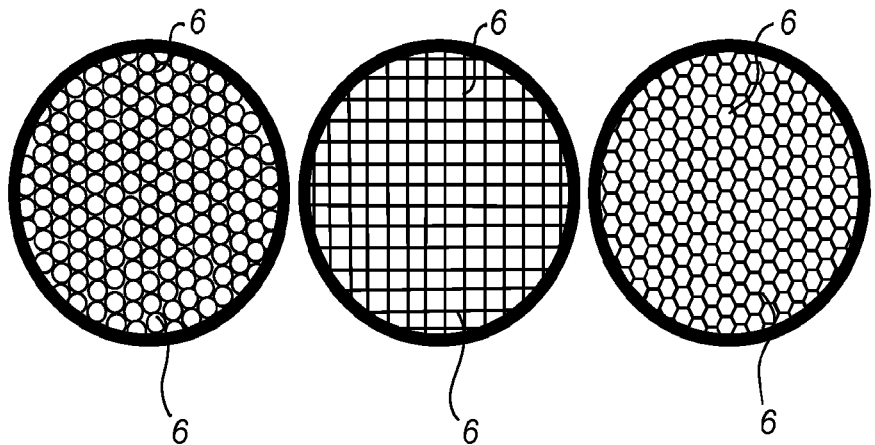
*Fig. 2a*   *Fig. 2b*   *Fig. 2c*
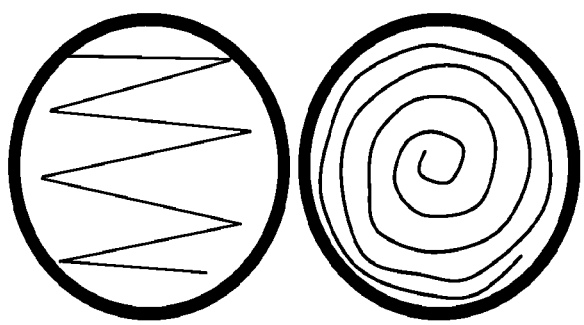
*Fig. 2d*   *Fig. 2e*

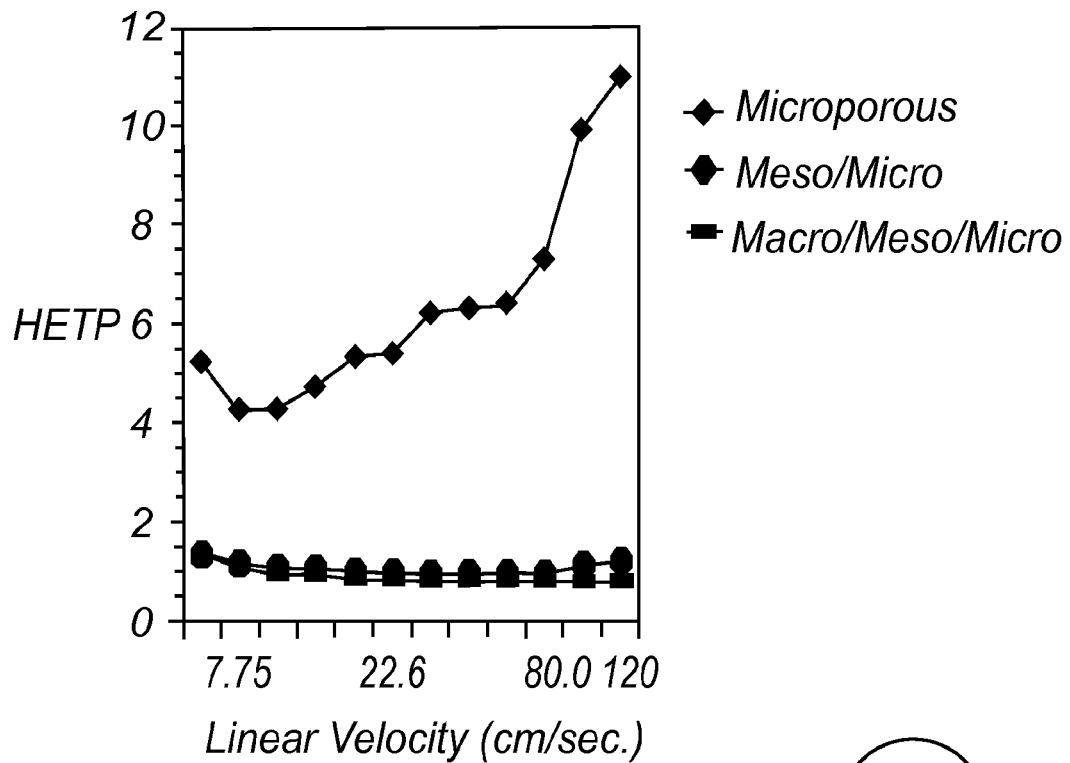
Fig. 3
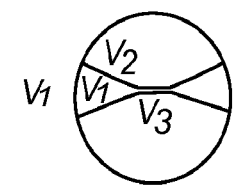
$v_1$ = interparticle velocity
 = macropore velocity
$v_2$ = mesopore velocity
 ~0.1 $V_1$
$v_3$ = micropore velocity
 ~0.01-0.001 $V_1$

METHOD FOR ACTIVE OR PASSIVE SAMPLING OF PARTICLES AND GAS PHASE ORGANIC AND NON-ORGANIC COMPONENTS IN A FLUID FLOW

TECHNICAL FIELD OF THE INVENTION

The present invention relates to an improved method for sampling of particles and gas phase organic and non-organic components in a fluid flow, and to a sampling device for use in the method.

BACKGROUND ART

There is a continuous demand for the monitoring of air-borne compounds that may have health effects on exposed individuals. A great interest exists for compounds that have occupational exposure limit values, set by governmental bodies, to ensure that the levels of such compounds are satisfactory low. In many cases it is not known what the air contaminants consist of, and for this reason it is of interest to learn more details about the nature of these "unknown" compounds and to reveal the identity of the most predominate ones. Another field of interest is to study and check the effect of measures with a view to reducing these levels in air, e.g. to check the "true" ventilation efficiency or other measures to control the air levels. Devices for this purpose can also be used for the monitoring of the quality of compressed air and air in respiratory protective devices. Other fields of application for such devices are e.g. the control of different volatile compounds present in food. Such compounds can be used as markers for degradation of certain food components or to monitor raw materials to ensure a satisfactory quality. Such devices may also be used to ensure that other compounds have not contaminated food. In hospitals such devices can be used to check the air levels of e.g. narcosis gases and to ensure that the personnel, patients and others are not exposed to toxic levels. Chemical warfare agents are also compounds that need to be checked for in order to reveal the presence thereof and to ensure that individuals are not exposed.

In environmental analysis there is a need to monitor the quality of air in cities, public places and in the nature or other environments. One purpose is to obtain background data for statistical studies and to check if the levels are below the levels set by national and international bodies. Such devices can also be used to check if the emission of industrial pollutants results in exposure in the nature or in populated areas. The achieved data can have an impact on decisions and interpretation of a certain situation. There is therefore a demand of a satisfactory high quality of the data.

There are many examples of air pollutants that occur in both gas and particle phase. Of special interest are the size fractions that have the ability to reach the lower respiratory tract. There are reasons to believe that the toxicology is different depending on not only the chemistry as such but also on the distribution on different target organs in the body of humans. There is a need to know more about the exposure to the respirable particle fraction present in air. In some cases it is also of interest to determine the identity and amount of inhalable particles, i.e. particles having the ability to pass the nose and the mouth when breathing in, and in some cases the identity and amount of particles that can reach the lungs and lower airways, i.e. particles having the ability to pass through the larynx when breathing in.

Numerous devices exist for the monitoring of air-borne compounds and there is a great variety of technology used.

In principle, the devices can be grouped in selective and non-selective devices. Non-selective devices give a response for several compounds and do not differentiate between two or several compounds and may also result in false positive results. Such devices are today still used, possibly due to the low cost. In many applications, false positive results can give rise to a high cost for the user, if costly measures are performed from invalid data.

Selective devices give a certain response for a selected compound or a group of compounds. Other present compounds do not interfere with the result. The frequency of false positive results will be much less as compared to non-selective monitoring. The quality of the data obtained is essential. Typical factors that describe the quality of the data are: repeatability, reproducibility, linearity (calibration graph characteristics with intercept and background), detection limit and quantification limit. In addition, knowledge regarding the interference from other compounds is necessary. It needs to be mentioned that a certain compound can influence the result even if the compound does not itself give rise to a response.

Similar techniques for the detection of air-borne compounds involves the use of e.g. photo ionisation detectors (PID, Thermo Scientific, Franklin, Mass., USA), flame ionisation detectors (FID, Thermo Scientific, Franklin, Mass., USA), infrared detectors (IR), portable gas chromatography (GC)-PID (PID Analyzers, Pembroke Mass., USA), portable GC-mass spectrometers (MS, Inficon Inc., New York, USA), GC-DMS ((Differential Mobility Spectrometry), Sionex Inc., Bedford, Mass., USA). All techniques give a response for a certain analyte, but to know the concentration the response needs to be translated into concentration by using information from a more or less sophisticated calibration curve. For many of the above techniques, the response varies with time due to ageing, contamination of the detector (reduces the signal) and other variables.

The GC-DMS technique mentioned above is used in the MicroAnalyser instrument (Sionex Inc., Bedford, Mass., USA). The GC-DMS technique is based on GC separation, with regards to compound volatility, in combination with the separation in a DMS sensor, with regards to other molecular properties such as size shape, charge etc.

There are several drawbacks with the present types of instruments. For PID and FID, identification of the individual chemicals is not possible. PID and FID detectors measure the sum of VOC (Volatile Organic Compounds). Infrared detectors suffer from problems with inferences. IR detectors are not possible to use when monitoring VOCs at low concentration when other interfering compounds are present.

Polyurethane (PUR) products as air pollutants are of particular interest to monitor and analyze. They frequently occur in industry, in particular in manufacturing and handling polyurethane foam, elastomers, adhesives and lacquers. Polyurethane is produced by the reaction of a bifunctional isocyanate with a polyfunctional alcohol. The satisfactory technical qualities of polyurethane have resulted in a large increase of its use and application fields during the last decades. In connection with thermal decomposition of polyurethanes, however, the formation of isocyanates, aminoisocyanates, anhydrides, and amines might occur, and extremely high contents can be found in air, e.g. when welding automobile sheet steel. Besides the known types of isocyanate, also new types of aliphatic isocyanates have been detected, in connection with e.g. heat treatment of car paint. Most of the isocyanates formed have been found to be represented by so-called low-molecular isocyanates. During short periods of time (peak exposure) particularly high isocyanate contents can be present, as is the case, for instance, when welding. Of all the dangerous substances on the limit value list, isocyanates have the lowest permissible contents. Exposure to this new type of isocyanates was previously unheard of. Isocyanates in both gas and particle phase have been detected in connection with welding, grinding and cutting of painted automobile sheet steel, and particles that can reach the lungs and lower airways in high contents containing isocyanates have been detected. In thermal decomposition products of painted automobile sheet steel, detection has been made of, among other things, methyl isocyanate (MIC), ethyl isocyanate (EIC), propyl isocyanate (PIC), phenyl isocyanate (Phi), 1,6-hexamethylene diisocyanate (HDI), isophorone diisocyanate (IPDI), 2,4- and 2,6-diisocyanate toluene (TDI) and 4,4-methylene diphenyl-diisocyanate (MDI).

In thermal decomposition of phenol/formaldehyde/urea-(FFU)-plastic, isocyanic acid and methyl isocyanate are formed. FFU plastic is used, among other things, in wood glue and as a binder in mineral wool (and bakelite), which is frequently used as insulation for ovens and furnaces in industrial and domestic use. New fields of application in which exposure to isocyanates has been detected are the soldering and processing of printed circuit boards in the electronic industry, the welding, grinding and cutting of painted sheet steel in the automobile industry and the welding of lacquered copper pipes. Isocyanates have a varying degree of toxicity to the organism depending on their chemical and physical form. As a result, the hygienic limit values have been set at an extremely low level in all countries. For the exposed individual, the degree of exposure to isocyanates varies considerably in different operations during a working day and in connection with breakdowns. Thermal decomposition products from PUR constitute a special problem, since new and completely unknown isocyanates are formed, whose toxicity has not yet been analyzed in a satisfactory manner. Furthermore, the increasingly sophisticated measuring methods have revealed exposure to isocyanates in an increasing number of operations in industry.

To sum up, there are a number of operations in numerous working areas where people are daily exposed to or at risk being exposed to isocyanates at a varying degree. Considering the ominous tendency of isocyanates to cause respiratory diseases and the fact that there are some carcinogenic substances among the thermal decomposition products of polyurethane, e.g. 2,4-diamine toluene (TDA), 4,4-methylenediamine (MDA) and MOCA, it is very important to measure in a reliable, sensitive and rapid manner any presence of isocyanates, but also other decomposition products dangerous to health, in environments where there is such a risk.

There is also a particular interest to monitor and analyze such solid/liquid air pollutants as, bacteria, oil mist components, allergens and fungi gaseous organic compounds to analyze are benzene, inorganic gases, volatile organic compounds, chemical warfare agents, anesthetic agents, isocyanates, isocyanic acid (ICA) methyl-isocyanate (MIC), ethyl isocyanate (EIC), propyl isocyanate (PIC), phenyl isocyanate (Phi), 1,6-hexamethylene diisocyanate (HDI), isophorone diisocyanate (IPDI), 2,4- and 2,6-diisocyanate toluene (TDI) and 4,4-methylene diphenyldiisocyanate (MDI), asbestos, dust and metals.

There is also a need to monitor and analyse certain chemical substances present in liquids, e.g. drinking-water, and flows in connection with purification plants. In such cases the liquid flow is transported through a sampling device in which the chemical to analyze is adhered to a specific reagent immobilized within the sampling device, e.g. in a filter and/or on the inner walls thereof, as well as in clean water, waste water, and food.

A sampling device for analysis of air pollutants, more precisely poluretane products, is disclosed in WO 00/75622, and further developments thereof are disclosed in WO 2007/129965, WO 2011/108981, and in WO 2014/193302. The sampling devices, also called samplers, disclosed in these publications collect the probed chemical in a two-step process. A fluid, i.e. a gas or a liquid, in which the amount of a chemical is to be measured, is pumped through the sampling device using a controlled flow. The chemical substance of interest present in the gas phase of the fluid is collected in an adsorption tube using a reagent coated on the surfaces present inside the tube. The flow of fluid is further pumped from the adsorption tube to and through a filter impregnated with the same reagent. The chemical substance in solid form or adhered to particles in the fluid is collected in the filter. After the measurements have been performed, the sampling device is sealed and is shipped to a laboratory for analysis of the amounts of chemical substance collected during the measurements.

It is known to use zeolites in adsorbent tubes, e.g. up to two long steel pipes, for capturing gas phase analytes in fluid flows, but these are not problems with the absorptive capacity.

It is also known that the inner walls of sampling tubes, also called denuders, which may be defined as any devices used to separate a gas from an aerosol, of sampling devices may be coated with carbon particles having the ability to collect and absorb gas phase components, e.g. benzene, in the sampled air flow.

It is also known to provide one or more different reagents on the surfaces of the carbon particles, said reagents having the ability to specifically react with the gas phase components. Sampling tubes which are completely filled or packed with absorbent particles, e.g. carbon particles, for the above-mentioned purpose are also known, also where the surfaces of the sorbent particles are provided with reagents. In such sampling tubes the gas phase compounds bound to the surfaces of absorbent particles or reacted with the reagents provided on the surfaces of the absorbent particles, are then released for subsequent analysis steps via thermal desorption.

The shortcomings and drawbacks with these kinds of known sampling devices are that gas phase compounds are bound to the sorbent, or the reagent provided on the sorbent, with a non-optimal specificity. Up to 90% of the gas phase components in a fluid flow should be captured, but this is not the case with most sampling devices presently used.

Another problem is that water present in the fluid flow to analyze is accumulated or captured as moisture inside the adsorbent tube or denuder, which then creates problems with the sampling capacity. Further, most sampling devices of this kind are difficult to manufacture in a reproducible way, and they are also relatively fragile to handle.

There is also an interest in providing a method of determining the identity and content of respirable and/or inhalable particles in a specific fluid flow, in particular a fluid flow comprising oil mist or vapor, in a more accurate way than so far known. Presently used methods for such a particle exposure assessment are not accurate enough for determining the amount and identity of respirable and/or inhalable particles due to the fact that the particle fraction and the gas phase fraction occur in the same air volume as they cannot distinguish between the two fractions. Further, when collecting particles there may be further release of volatile components from the trapped particles and this will result in the underestimating on the total air borne particles. Further, the pressure drop of the denuder sampler is much less as compared to the sampling in packed beds of particles.

Thus, there is need of an improved sampling method and sampling device for determining the identity and the amount of respirable particles in a fluid flow, and for determining the identity and amount of specific hazardous or otherwise undesired substances in a fluid flow.

BRIEF DESCRIPTION OF THE DRAWINGS

FIG. 1 a)-d) shows schematically different embodiments of a sampling device used in the method according to the present invention.

FIG. 2 a)-e) shows different cross-section forms of the channel and elements provided in a denuder device used in the method according to the present invention.

FIG. 3 shows a diagram of velocity vs. HETP for carbon molecular sieves.

SUMMARY OF THE INVENTION

Figure 4:
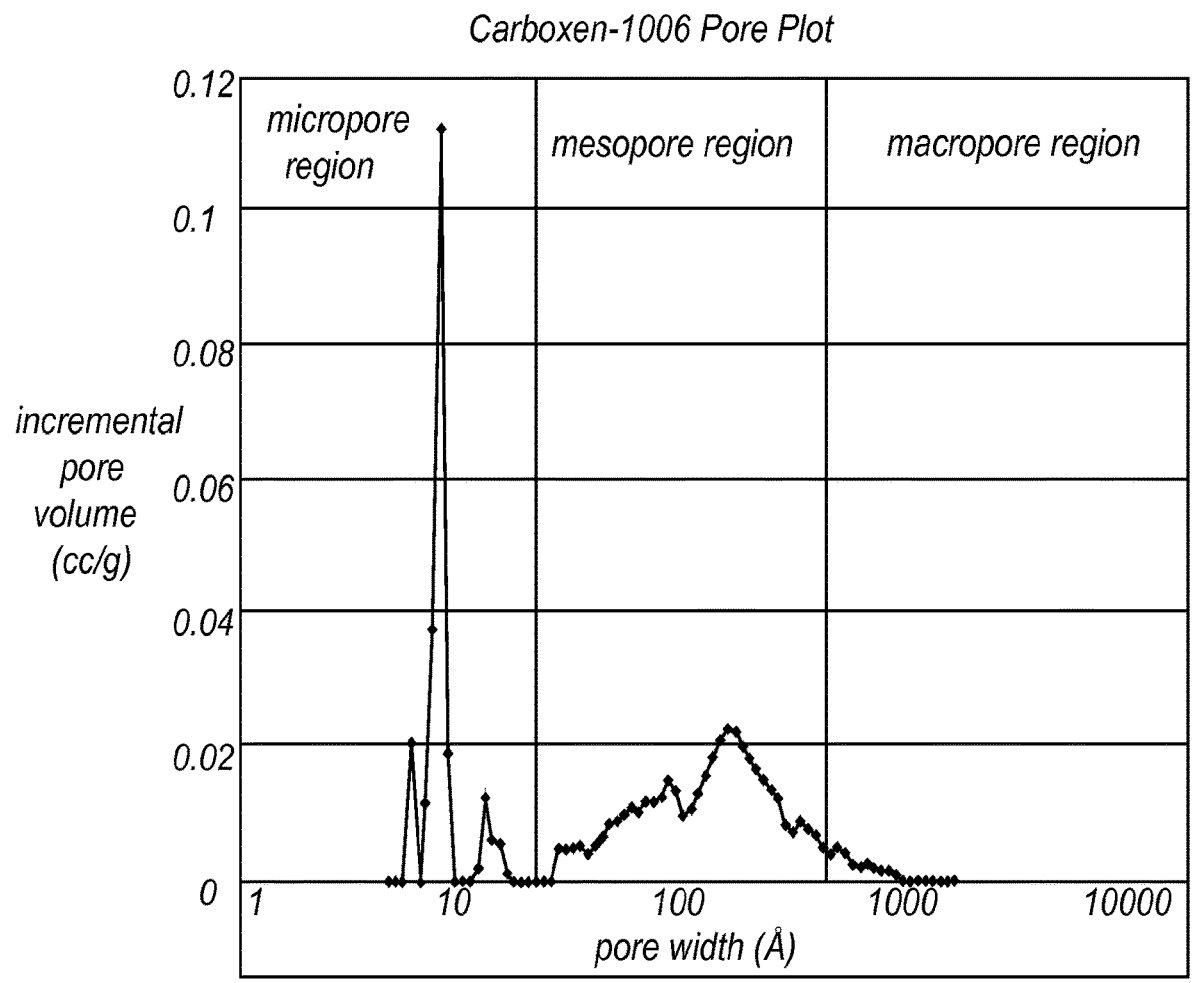
FIG. 4 shows a diagram illustrating the pore structure of a multi-porous carbon molecular sieve.

An object of the present invention is to provide an improved sampling method by which the above-mentioned problems are solved and the above-mentioned needs are fulfilled.

This object is achieved with a method according to claim 1. The object is also obtained with a sampling device according to the independent product claim. Particular and preferred embodiments are disclosed in the subsequent dependent claims.

In one aspect the present invention relates to a method for active or passive sampling of particles and gas phase organic and non-organic components in a fluid flow (4), wherein
 a) a sampling device comprising a first denuder device (1), a filter device (3), and a second denuder device (2), arranged in axial direction in a series in said order, is provided at a measurement spot, wherein the first denuder device (1) and the second denuder device (2) each is hollow and contains surfaces provided with a hydrophobic and/or a hydrophilic sorbent, or said second denuder device (2) contains a packing of hydrophobic and/or hydrophilic sorbent particles,
 b) the fluid flow (4), which contains gas phase organic components, gas phase non-organic components, and particles, optionally having gaseous organic and/or non-organic components bound thereto, is introduced in the sampling device during a predetermined time period,
 c) gas phase organic and/or non-organic components are bound to the hydrophobic and/or hydrophilic sorbent in the first denuder device (1), and the particles are allowed to pass through the first denuder device (1) and to enter the filter device (3), wherein,
 d) particles having a diameter exceeding a certain limit value are captured in the filter device (3), and wherein any gaseous organic and/or non-organic components bound to said captured particles in the filter device (3) are released therefrom,
 e) particles having a diameter which is lower or equal to said limit value, and said any gaseous organic and/or non-organic components released from the particles captured in the filter device (3) are allowed to enter the second denuder device (2) and are bound to the hydrophobic and/or hydrophilic sorbent therein,
 f) gas phase organic components bound in the first denuder device (1) are released from the hydrophobic sorbent therein by thermal desorption, and wherein the particles and the gaseous organic components bound in the second denuder device (2) are released from the hydrophobic sorbent therein by thermal desorption,
 g) wherein gas phase non-organic components bound in the first denuder device (1) are released from the hydrophobic and/or hydrophilic sorbent therein by chemical extraction,
 h) wherein the particles and the gaseous organic and/or non-organic components bound in the second denuder device (2) are released from the hydrophobic and/or hydrophilic sorbent by chemical extraction, and
 i) the identity and amount of particles having a diameter which is lower or equal to said limit value, as well as the identity and amount of gaseous organic and/or non-organic components, is determined for the predetermined time period and the fluid flow rate (4).

In another aspect the present invention the present invention relates to a sampling device for active or passive sampling of particles and gas phase organic and non-organic components in a fluid flow (4), wherein said sampling device comprises a first denuder device (1), a filter device (3), and a second denuder device (2), arranged in axial direction in a series in said order, optionally also a pre-selector device (5) arranged between the first denuder device (1) and the filter device (3) or before the first denuder device (1), wherein the first denuder device (1) and the second denuder device (2) each is hollow and contains surfaces provided with a hydrophobic and/or a hydrophilic sorbent, or said second denuder device (2) contains a packing of hydrophobic and/or hydrophilic sorbent particles, and wherein each sorbent optionally is provided with a reagent specific for said particles and/or gas phase organic and non-organic components to sample.

Specific embodiments of the present invention are defined in the dependent claims.

Detailed Description of the Present Invention and Preferred Embodiments Thereof First, some expressions present in the application text will be defined.

The expression "inhalable" used throughout the application text in connection with particles is intended to mean that the particle has such a size that it can pass the nose and the mouth when breathing in. Per definition, an inhalable particle has a maximum width of 100 µm.

The expression "thoracic and respirable" fractions used throughout the application text, are defined as the fraction of inhaled particles capable of passing beyond the larynx and ciliated airways, respectively, during inhalation.

The expression "respirable" used throughout the application text in connection with particles is intended to mean that the particle has such a size that it has the ability to reach the alveoli in the lungs. Per definition, an inhalable particle has a maximum width of 4 µm.

The expressions "gas phase organic components" and "organic gas phase components" interchangeably used throughout the application text is intended to mean organic components present in gaseous form in the gas phase in the original fluid flow to analyze.

The expressions "gas phase non-organic components" and "non-organic gas phase components" interchangeably used throughout the application text is intended to mean non-organic components present in gaseous form in the gas phase in the original fluid flow to analyze.

The expression "gas phase components" used throughout the application text is intended to mean both organic and non-organic components present in gaseous form in the gas phase in the original fluid flow to analyze.

The expressions "gaseous organic and non-organic components" and "organic and non-organic gaseous components" interchangeably used throughout the application text is intended to mean organic and non-organic components which normally exist in gaseous form but which are bound to the particles present in the original fluid flow to analyze. Said gaseous organic and non-organic components are released from the particles captured in the filter device 3. Some of the gas phase organic components and some of the gaseous organic components may be identical. The same applies in view of the gas phase and gaseous non-organic components, respectively.

The expression "fluid flow" used throughout the application text is intended to mean a flow of a gas or a liquid, which also may contain components in solid form, e.g. fluidized particles and aerosols. One example of a fluid is an air flow containing small particles having the substances to analyze bound to their surfaces. Another example of a fluid flow is a water flow containing the substances to analyze, e.g. a drinking water flow, and flows in connection with purification plants.

The expression "fluid flow direction" used throughout the application text is intended to mean the axial direction in relation to the cross-section of the components of the adsorption device.

The expression "component" used throughout the application text is intended to mean a chemical compound or substance of any kind which is of interest to sample or analyze.

The expression "one or more reagents" used throughout the application text is intended to mean that more than one type of reagent may be used when more than one type of component in the fluid flow is to be analyzed. In the following, the expressions "reagent" or "reagents" are sometimes used for simplicity reasons, but is nevertheless intended to mean "one or more reagents", unless otherwise is indicated or appears from the context.

The expression "particles" used throughout the application text is intended to mean solid or liquid components of any form.

The expression "aerosol" used throughout the application text is intended to mean a mixture of gas and particles.

The expression "hydrophobic" used throughout the application text is intended to mean a compound or a surface that is water repellent.

The expression "hydrophilic" used throughout the application text is intended to mean a compound or a surface that have a strong affinity to water.

The expression "sorbent" used throughout the application text is mainly intended to mean the sorbent particles present on the inner surfaces of the first and second denuder device 1 and 2, respectively, while the expression "sorbent particles" mainly is intended to mean the particles of sorbent packed in the second denuder 2.

The expression "passively" and "passive transport" used throughout the application text is mainly intended to mean transport by diffusion of a gas or very small particles.

The expression "actively" and "active transport" used throughout the application text is mainly intended to mean transport by active flow transport using suction or pressure of gas and particles.

The present invention will now be disclosed in connection with the Figures.

In the method according to the present invention a fluid flow 4 is introduced in a sampling device, as is shown in FIG. 1a during a predetermined period. The fluid flow 4 may be any kind of air-based flow containing particles, aerosols, and gas components of interest to analyze, wherein said gas components may be present in gaseous form in the gas phase of the fluid flow and/or be present inside or on the surface of said particles. A fluid flow of particular interest to sample is a flow of oil mist or vapor containing both a gas phase and a particle phase.

With the method according to the present invention any organic and non-organic components in gaseous form in the fluid flow may be analyzed, i.e. be determined in view of identity and amount.

There is also a particular interest to monitor and analyze oil mist or vapor, industrial wastes, contaminated water, industrial emissions, indoor and outdoor air, inorganic gases, bacteria, oil mist components, allergens, fungi, spores and other biological compounds, gaseous organic compounds like benzene, such solid or liquid air pollutants as bacteria, inorganic gases, asbestos, dust and metals, volatile organic compounds (VOC), chemical warfare agents, anesthetic agents, isocyanates, such as aromatic isocyanates, small aliphatic iso-cyanates like butylisocyanate (BIC), propylisocyanate (PIC), iso-propylisocyanate (i-PIC), ethylisocyanate (EIC), methylisocyanate (MIC), and isocyanic acid (ICA.), but also aminoisocyanates, and isothiocyanates. Further examples are anhydrides, ammonia (NH3), aliphatic and aromatic amines: [dimethylamine (DMA) n-butylamine (n-BA), methylene dianiline (MDA), p-phenylene diamine (PPD), 2,4 and 2,6-toluene diamine (TDA), alfa- and beta-naphtylamines trimethylamine (TMA)]; diisocyanates: cyclohexyl diisocyanate (CNDI), hexamethylene diisocyanate (HDI), dicyclohexyl metan diisocyanate (HMDI), IEM, isophorone diisocyanate (IPDI), 4,4"-methylene diphenylisocyanate (MDI), naphtyldiisocyanate (NDI), paraphenylene diisocyanate (PPDI), 2,4- and 2,6-toluene diisocyanate (TDI), trimethylhexamethylene diisocyanate (TMDI), trimethyl xylene diisocyanate (TMXDI), xylenediisocyanate (XDI); hydrazines: monomethylhydrazine (MMH), hydrazine ($N_2H_4$,), and 1,1 dimethylhydrazine (DMH). Other examples of substances or compounds to analyze are hydrides: arsine ($AsH_3$), diborane ($B_2H_6$), disilane ($Si_2H_6$), germane ($GeH_4$), hydrogen selenide ($H_2Se$), phosphine (PH3), silane ($SiH_4$), stibine ($SbH_3$), tert-butylarsine (TBA), tert-butylphosphine (TBP)], hydrogen cyanide (HCN), hydrogen sulfide ($H_2S$), mineral acids: [hydrogen bromide (HBr), hydrogen chloride (HCl), hydrogen fluoride (HF), hydrogen Iodide (HI), nitric acid ($HNO_3$), sulfuric acid ($H_2SO_4$)], oxidizers: [bromine ($Br_2$), chlorine ($Cl_2$) II, chlorine dioxide ($ClO_2$), hydrogen peroxide ($H_2O_2$), nitrogen dioxide ($NO_2$), ozone ($O_3$)], phosgene ($COCl_2$), sulfur dioxide ($SO_2$)].

The fluid flow 4 is introduced in the inlet of the sampling device shown in FIG. 1a used in the method according to the present invention. The sampling device comprises a first denuder device 1, a filter device 3, and a second denuder device 2. These components are arranged in the axial direction of the fluid flow 4 and in a series in the above listed order of devices. Further, these components are tightly sealable to each other with a view to avoiding leakage of any components out from the sampling device. Said first denuder device 1 is hollow in its axial direction and contains several axially directed channels 6 each having inner surfaces provided with hydrophobic and/or hydrophilic sorbents in a particle form.

The inner surfaces of the first denuder device (1) may be provided with particles of one or more different kinds of sorbents which may be exclusively hydrophobic, exclusively hydrophilic, or both hydrophobic and hydrophilic. In the case of exclusively hydrophobic sorbents, only hydrophobic components in the fluid flow (4) are bound to the hydrophobic sorbents, while hydrophilic components in the fluid flow (4) passes through the first denuder (1). The corresponding case applies in the case of exclusively hydrophilic sorbents.

Single-walled carbon nanotubes are typically chemically inert. Covalent attachment of molecular species to fully sp2-bonded carbon atoms on the nanotube sidewalls has been proved to be difficult. Adsorbing molecules to nanotubes via non-covalent forces, however, turns out to be facile and has important consequences to their physical properties and potential applications (Carbon Nanotubes: Synthesis, Integration, and Properties HONGJIE DAI* Department of Chemistry, Stanford University, Stanford, Calif. 94305, Received Jan. 23, 2002 ACCOUNTS OF CHEMICAL RESEARCH/VOL. 35, NO. 12, 2002).

Carbon in nano-tubes are typically hydrophobic. However, hydrophilic properties can be accomplished in several ways. Carbon nanotubes are metallic or semiconducting, based upon delocalized electrons occupying a 1-D density of states. However, any covalent bond on SWNT (Side Wall Nano Tubes) sidewalls causes localization of these electrons. In the vicinity of localized electrons, the SWNT can no longer be described using a band model that assumes delocalized electrons moving in a periodic potential. Two important addition reactions of SWNT sidewalls are: (1) Fluorination, and (2) aryl diazonium salt addition. These functional groups on SWNT improve the solubility and processability. Moreover, these reactions allow for combining unique properties of SWNTs with those of other compounds. Above all, the selective diazonium chemistry can be used to separate the semiconducting and metallic nanotubes. [http://en.wikipedia.org/wiki/Selective_chemistry_of-_single-walled_nanotubes]

Thus, in the first denuder device (1) there may be a mixture of sorbents which are hydrophilic and/or hydrophobic. Thus, the arrangement of sorbents in the first denuder device (1) may be tailored with a view to binding or capturing a battery of different specific gas phase components of interest to analyze in the fluid flow (4). Depending on the character of such an arrangement, some gas phase components which may be organic or non-organic, hydrophilic or hydrophobic, may pass through the first denuder device (1) without being bound. Further, the specificity of the sorbents may be further influenced by making them acidic or alkaline. This also influences the gas phase components to be captured in the first denuder device (1).

All kinds of combinations of sorbents in view of hydrophilic/hydrophobic properties and acidic/alkaline properties for binding of organic/non-organic components are possible. In principle, the first denuder device (1) may be prepared in such a way that only particles passes through, while all other components in a certain fluid flow (4) are bound.

The sorbents may also be provided with a reagent having specific reactivity with the organic or non-organic gas phase component to bind. A mixture of one or more different reagents bound to the sorbents may be used with a view to binding several different organic and/or non-organic gas phase components present in the fluid flow (4). Said one or more reagents may have been bound to the sorbent by e.g. hydrophilic or hydrophobic interaction or ion pairing etc and react specifically with the gas phase organic and/or non-organic components in the fluid flow 4, wherein a reaction product bound to the sorbent is formed. The reason for using reagents is that the binding to the sorbent may be facilitated, that the compounds of interest are stabilized, and that a subsequent analysis of the reaction product is facilitated compared to analysis of the gas phase organic and/or non-organic components as such. The reaction product may also be stabilized against oxidation, reduction and further reactions.

In one embodiment some of the sorbents in the first denuder device 1 are provided with reagent, while some are not, depending on the nature of the gas phase components of interest to capture. E.g., for the analysis of benzene no reagent is required.

As to the reagents used in the inventive method, these should have the ability to specifically bind to any one of the components of interest to analyze in the fluid flow 4. Specific reagents used are e.g. gold for the reaction with mercury, one or more primary or secondary amines, e.g. dibutylamine (DBA), for the reaction with isocyanates and anhydrides, acidic reagents for the reaction with amines to form ion-pairs, alkaline reagents for the reaction with acids to form ion-pairs, and hydrazines to form hydrazones with aldehydes or ketones.

The overall cross-section form of the hollow first denuder device 1 in FIG. 1*a* is not critical and may vary between different two-dimensional geometrical forms, but is in a useful embodiment circular. The amount of channels 6 may vary between e.g. 1 and 30 for a cross section of 3 mm, and depends on the cross-section size of each channel 6. Examples of some channels 6 with different cross-sections are shown in FIG. 2 *a*)-*c*). The cross-section of each channel 6 is not critical, and examples of useful cross-section embodiments are a circular (FIG. 2 *a*)), quadratic (FIG. 2 *b*)), and hexagonal or honey comb (FIG. 2 *c*)) cross-section. When the channels 6 have a circular cross-section they have the form of tubes arranged in parallel in the first denuder device 1. The channels 6 in the one and same first denuder device 1 may all have the same cross-section, or may have a mix of cross-sections, e.g. a mix of those exemplified above.

In the case the channels 6 have a circular cross-section, void volumes arises when the cylindrically formed channels 6 are packed within the first denuder device 1. In such a case, also the outer surfaces of the channels 6 facing said void volumes may be provided with the sorbent. This also applies in the case of other channels 6 having cross-section variants leading to void volumes when the channels 6 are packed within the first denuder device 1. In one embodiment the whole arrangement of channels 6 present within the first denuder device 1 is manufactured integrally in one piece, e.g. as a cylindrically formed ceramic block containing several channels.

The hydrophobic and/or hydrophilic sorbent arranged on the inner surface of each channel 6 is provided as a layer on said inner surface. The whole or parts of the inner surface of each channel 6 may be provided with said sorbent. The inner diameter of each channel 6 in the embodiment with a circular cross-section is 0.01-10 mm. The diagonal distance between the inner walls in each channel 6 having a quadratic cross-section is 0.01-10 mm, and the distance between opposite inner walls in the embodiment with a hexagonal cross-section is 0.01 mm-10 m.

In one embodiment the sorbent comprises carbon particles, e.g. manufactured of synthetic carbon in spherical or tubular form. In another embodiment the carbon particle comprises graphene. Alternatively, or as a complement, hydrophobic sorbents, such as plastic polymers, or spherical silica particles with a surface layer of polymers or organic molecules may be used. In the first denuder device 1 the inner surface of each channel 6 may be provided with at least one layer of carbon particles each having a critical size of 10 nm-1 mm, preferably 100-50 000 nm.

When the inner surfaces of the channels 6 are provided with carbon particles, the cross-sectional inner dimensions disclosed above are almost the same due to the small size of the carbon particles. Several channels 6 having different inner dimensions, such as different cross-sections and different distances between their inner surfaces, may alternatively be packed in the first denuder device 1. However, channels 6 having the same inner dimensions, i.e. the same cross-sections and the same distances between their inner surfaces, are more useful in some embodiments. Further, the free passage in the center of each channel 6 provided with a sorbent layer on its inner surface has to be big enough for allowing passage of particles in the fluid flow 4. The sorbent may also be arranged on a support provided on the inner surface of the first denuder device 1. Examples of such supports are metal such as aluminum, ceramics glass, etc. The reason for the presence of such a support is that it facilitates the attachment of the carbon particles within the first denuder device 1, and that the denuder geometry is arranged and fixated. The length of the first denuder device 1 may be 1-50 cm, and the outer diameter may be 0.1-10 cm. In one embodiment the length is 10 cm and the outer diameter is 0.8 cm.

Carbon particles useful in the inventive method can e.g. be purchased from Cheaptubes.com.

The inventive sampling device provided with the first denuder device 1 containing the specific hydrophobic carbon particle sorbent disclosed above has surprisingly turned out to be more effective than so far known sampling devices in that adsorption of gas phase organic components is increased to more than 95% and that negligible amounts of water are captured in the first denuder device 1.

The reason why this specific embodiment of sorbent shows superior and surprising results compared to conventional carbon-containing sorbents is that they contain the specifically designed graphitized carbon particles or carbon molecular sieves leading to an increased adsorbing ability due to the fact that the surface area/weight is high and that they repel water molecules to a substantially higher extent due to absence of e.g. metals and ions.

In another embodiment of the hollow first denuder device 1 the channels 6 are replaced with one or more elements extending in the axial direction of the first denuder device 1. Said elements may be planar constructions, e.g. formed like a paper, which e.g. have been folded, bent, rolled up, or arranged to another useful form. FIG. 2*d* shows schematically in cross-section a first denuder device 1 provided inside with such an element having a zigzag cross-section form, and FIG. 2*e* shows schematically in cross-section a first denuder device 1 provided inside with such an element having a spiral-like cross-section form. Sorbents are bound to the surfaces of said elements, thereby providing a large accessible binding surface. In this embodiment the inner surface of the first denuder device 1 surrounding said elements may also be provided with sorbents.

The fluid flow 4 may be allowed to passively pass through the first denuder device 1 without any active measure from the operator, i.e. just using diffusion or convection of the air flow at the measurement spot. Thus, the fluid flow passes the sampling device via a so-called passive transport. The sampling device may e.g. be placed at a measurement spot at which there is a "natural" draw of a flow. Thus, just a diffusion of the fluid flow 4 is enough for performing the analysis method according to the present invention. This is an advantage compared to known techniques.

The fluid flow 4 may alternatively be allowed to actively pass through the first denuder device 1, i.e. via a so-called active transport. Different measures may alternatively be taken for more or less forcing the fluid flow 4 through the sampling device, but such an alternative involves the addition of complementary equipment, e.g. pumps, and thereby increased costs. One advantage with active transport is that substantially more particles, up to approximately 100-10 000 times, may be collected in the filter device 3.

When the fluid flow 4 is allowed to pass through the first denuder device 1, some of the organic and/or non-organic components present in the gas phase of the fluid flow 4 are bound or absorbed to the hydrophobic and/or hydrophilic sorbents in the first denuder device 1, depending on the specific arrangement of different sorbents and any reagents bound to said sorbents in the first denuder device 1. Particles present in the fluid flow 4 passes through the first denuder device 1 without being absorbed or captured by the sorbents. Some of these particles may have gaseous, but also non-gaseous organic and/or non-organic components bound on the inside or onto the surface thereof, but these organic and/or non-organic components are not available for being bound to or absorbed by the sorbents in the first denuder device 1. The reason is that the particles do not diffuse and will strictly follow the fluid flow stream.

In the filter device 3 particles having a diameter exceeding a certain limit value are captured. The value of the particle size diameter used in the filter device 3 is in one embodiment 4 μm in the case of respirable particles, and 10 μm in the case of inhalable particles. The filter device 3 may be any conventional filter having the ability to separate particles having different sizes into at least two different size-based fractions, but is in one embodiment a high-efficiency particulate arrestance (HEPA) filter. In another embodiment the filter device 3 may be an integrated filter holder having an outer diameter (OD) of 35 mm. Particles having a diameter which is higher than said limit value are captured in the filter device 3, while particles having a diameter which is lower than or equal to said limit value passes through the filter device 3 and are allowed to enter the second denuder device 2. Further, any gaseous organic and/or non-organic components bound within and/or on the surface of said captured particles in the filter device (3) are released by evaporation from said captured particles and are also allowed to enter the second denuder device 2.

In one embodiment the filter device 3 as such may contain several filtration sections in a series having different opening sizes in the axial direction for the capturing of further different fractions of particles within specific size intervals. After a measurement period, the filter device 3 may be replaced with a new one or is regenerated from captured particles before a new measurement period is initiated.

With a view to determining the amount of respirable particles in a specific fluid flow containing particles in a large span of particle sizes in an improved and more accurate way, a pre-selector device 5 may according to a further embodiment of the inventive method be arranged in the fluid flow direction in the sampling device, more precisely between the first denuder device 1 and the filter device 3. This embodiment is schematically shown in FIG. 1*b*. In another embodiment the pre-selector device 5 may be arranged before the first denuder device 1.

By use of the embodiment including a pre-selector device 5 clogging of too large particles in the filtration part or parts of the sampling device are avoided and the passage of the inhalable, thoracic, and/or respirable particles is facilitated. The pre-selector device 5 may have any d50 particle cut-off value in the interval 2-100 μm, which means that 50% of the particles having a size of a certain value within said interval will be collected in the pre-selector device 5. In one embodiment the d50 particle cut-off value is 4 μm. The pre-selector device 5 may be any device having the ability to separate particles with the basis on the sizes thereof. In one embodiment the pre-selector device 5 is a virtual impactor.

By e.g. using the virtual impactor the flow direction and the fluid flow speed are changed in said virtual impactor by passing the fluid flow 4 through a cone with a small nozzle. Thereafter, the fluid flow 4 is directed to an impactor plate to trap or capture said particles. The impactor plate may be a small plate where particles impact and are deposited. The particles may either be retained on the impactor plate or be transferred through a connected exit tube having a small exit flow, e.g. 1/10 of the main flow, with a view to separating particles larger than the cut-off size from the main flow stream within the sampling device. The d50 particle cut-off value of 4 μm has been set as the critical upper particle size limit value for a particle to be respirable. In the case of setting the corresponding upper limit for inhalable particles, the cut-off or limit value is 10 μm.

Thus, a first fraction of predominantly larger particles separated with the basis of the predetermined particle size calibration curve for a specific particle diameter limit value is captured in the pre-selector device 5. Optionally, the first fraction of particles may be taken out from the sampling device via an exit tube. If needed, the particles in said first fraction, as well as any gaseous organic and/or non-organic components bound inside or on the surfaces of the particles, may be analyzed separately by use of conventional techniques. A second fraction of predominantly smaller particles, which are of particular interest to analyze and which are not captured in the pre-selector device 5, are allowed to pass through the pre-selector device 5 and to enter the filter device 3. This also applies for any gas phase organic and/or non-organic components in the original fluid flow 4 which have not been captured in the first denuder device 1.

In one embodiment several pre-selection devices 5 may be coupled in a series, wherein each one is connected to a sampling device according to the present invention and delivers particle fractions having different size intervals.

The particles present in the second fraction of particles and having a diameter exceeding the specific limit value for the filter device 3 are captured in the filter device 3, wherein the particles present in the second fraction of particles and having a diameter which is lower or equal to said limit value passes through the filter device 3 and are allowed to enter the second denuder device 2. Thus, irrespective if a pre-selector device 5 is used or not, a fraction of particles separated from predominantly larger particles with the basis of the specific limit value for the filter device 3, is allowed to reach the second denuder device 2 together with any gaseous organic and/or non-organic components released from the inside and/or the surfaces of the particles captured in the filter device 3.

The same principles as to the construction and dimensions apply for the second denuder device 2 as for the first denuder device 1 disclosed above. The arrangement and character of the sorbents in the first and the second denuder device 1, 2 is normally the same, but may also differ. E.g., the sorbents in the first denuder device (1) may be exclusively hydrophilic and the sorbent particles in the second denuder device (2) may be exclusively hydrophobic at the same time, and vice versa. Normally, the same kind of sorbents is used in both the first and the second denuder device 1, 2. However, several combinations in view of hydrophilic/hydrophobic, and acidic/alkaline sorbents, with or without specific reagents, are also possible for the denuder devices 1, 2 with a view to capturing the relevant gas phase organic and/or non-organic components in the first denuder device 1 and the relevant gaseous organic and/or non-organic components, released from the inside or the surfaces of the particles captured in the filter device 3, in the second denuder device 2.

In one embodiment the second denuder device 2 is not hollow. Instead, it contains a packing of hydrophobic and/or hydrophilic sorbent particles. Such a packing provides a large accessible binding surface on the particles. In general, the packed sorbent particles in the second denuder 2 are larger compared to the carbon particles present in the first denuder device 1. The sorbent particles may be the same as the particles of sorbents arranged on the inner surfaces of the first denuder device 1 and in the hollow embodiment of the second denuder device 2, but not necessarily. Otherwise, the same combinations in view of different sorbents, hydrophobic/hydrophilic properties and acidic/alkaline properties as disclosed above also apply for this embodiment.

As appears above, the arrangement of the sorbent particles in the denuder devices 1, 2 influences the kind of components which exits the second denuder device. In some cases sorbents may have been inadvertently released from the surface of the first and/or second denuder 1 and 2, and in such cases certain unbound components may exit the second denuder 2. Other components originally present in the fluid flow 4 and present in the fluid flow exiting the second denuder device 2 are water, nitrogen dioxide, methane, helium, and nitrogen. Any side products formed in any chemical reaction, such as catalytic cleaning, in the sampling device may also be present in this exit fluid flow. This exit flow does in general not contain any particles at all, as the particles in the fluid flow are captured by the sorbent in the second denuder device 2.

In one embodiment of the method according to the present invention shown in FIG. 1*c* the fluid flow (4) is a gas flow. The method is performed with the sampling device without the first denuder device (1), wherein particles, gas phase organic and/or non-organic components (?), and gaseous organic and/or non-organic components are captured in the filter device (3) and in the second denuder device (2), and wherein cleaned liquid emits the sampling device. No analysis of the components is performed in this embodiment, as the main object is just to eliminate undesired components from the liquid flow.

In another embodiment using the same sampling device shown in FIG. 1*c* the main object is a total analysis, wherein particles, gas phase components, and gaseous components released from particles are analyzed in the same way as for other embodiments of the inventive method.

In still another embodiment of the method according to the present invention shown in FIG. 1*d* the fluid flow 4 is a pure liquid flow, preferably a water based flow. This method is performed with the sampling device lacking the first denuder device 1 and the filter device 3, wherein particles, gas phase organic and/or non-organic components dissolved in the liquid, and gaseous organic and/or non-organic components are captured in the second denuder device 2, and wherein cleaned liquid emits the sampling device. The analysis of the components of interest is performed as for the other embodiments.

In the second denuder device 2 the gaseous organic and/or non-organic components released from the particles entered are all bound to the hydrophobic and/or hydrophilic sorbents on the inner surfaces thereof or on the surfaces of the packed sorbent particles therein.

All of the components in the original fluid flow 4 of interest to analyze have been bound in the first and the second denuder device 1, 2, optionally as a reaction product after having reacted with a reagent. With a view to releasing all these components and particles bound to the sorbents in the first denuder 1 and the second denuder 2, these are subjected to different releasing steps depending on the kind of gas phase components and gaseous components bound in the sampling device. The following apply for the situations specified below.

When gas phase organic components are bound in the first denuder device 1, these are released from the hydrophobic sorbent therein by thermal desorption, and when particles and the gaseous organic components are bound in the second denuder device 2, these are also released from the hydrophobic sorbent therein by thermal desorption.

When gas phase non-organic components are bound in the first denuder device 1, these are released from the hydrophobic and/or hydrophilic sorbent therein by chemical extraction.

When the particles and the gaseous organic and/or non-organic components are bound in the second denuder device 2, these are released from the hydrophobic and/or hydrophilic sorbent by chemical extraction.

It is of a major interest to determine the identity and amount of particles having a diameter which is lower or equal to said limit value in the filter device 3, as well as the identity and amount of said gas phase organic and/or non-organic components, and said gaseous organic and/or non-organic components, for the predetermined time period and the fluid flow rate (4).

It is not known before to use thermal desorption for releasing gas phase organic or non-organic components bound to a sorbent provided on a surface in a denuder device. Before the thermal desorption step, the first and the second denuder device 1, 2 are separated from the sampling device.

The thermal desorption step is performed at a temperature adapted to the temperature at which the specific analyte, i.e. the gas phase organic component or the reaction product between this and a specific reagent, is released from the sorbent in the denuder. Normally, the temperature level is set to at most 230° C., preferably at most 190° C. In the case of e.g. benzene the desorption temperature is set to 190° C., at which the benzene molecules are released and collected for the subsequent analysis step. Thereafter, the temperature is increased to another level, at which it is known that another analyte of interest is released. The temperature during the desorption step may be incrementally increased up to approximately 230° C.

During the thermal desorption step the organic components and particles bound to the sorbents are released from the sorbent surface at different temperatures and are collected in a sample analyzer equipment system. Any conventional analysis method may be used, both for organic and non-organic analytes, and some examples are ICP-MS (Inductively Couple Plasma-Mass Spectroscopy) or atomic absorption spectrometry, GC-FID (Gas Chromatography-Flame Ionization Detection), GC-MS (Gas Chromatography-Mass Spectroscopy), LC-MS (Liquid Chromatography-Mass Spectrometry) or any other relevant analytical technique for organic or inorganic compounds, as well as weighing before and after the passage of the sampling device. In a preferred embodiment LC-MS (Liquid Chromatography-Mass Spectrometry) is used. Bioanalytical techniques, typically immunological methods, can also be utilized for determining bacteria, fungi or other bio-molecules, alternatively electro-chemical determination using e.g. electrophoresis or ion-exchange methodology.

The specific peaks shown in the plot after an LC-MS analysis then obtained represent specific components and particles originally present in the fluid flow, as well as any reaction products. As to the particles, both the identity and the amount may be deducted from the peaks in the plots and is more precisely determined by mass spectroscopy where the obtained mass spectra will reveal the identity.

If applicable, analysis results obtained for the components separated in and exiting the pre-selector device 5 may be included with a view to obtaining a total value for the analytes in the fluid flow 4.

The chemical extraction is performed in the case of releasing organic, biomolecules or non-organic components, either gas phase non-organic components captured in the first denuder device 1 or gaseous non-organic components, released from the particles in the filter device 3 and captured in the second denuder device 2. The chemical extraction is performed with organic or inorganic solvents.

Alternatively, the identity and the amount of specific organic or non-organic components in gaseous form during the predetermined time period may be determined without a thermal desorption step. Instead, the determination can be made by detecting the reaction product between the component to analyze and a reagent present on the sorbent. This can take place in both the first denuder device 1 and the second denuder device 2, and the sampling device does not need to be detached for such a measurement.

In the method according to the present invention the sampling device is regenerated by heating and purging it from said gaseous organic and/or non-organic components and particles previously captured in the first denuder device (1) and in the second denuder device (2).

EXAMPLES

Some examples of experiments performed with carbon molecular sieves involved in the present invention are disclosed below.

The use of a specific multi-channel tube useful in the present invention has increased the capacity of the denuder due to the presence of 9-12 channels which effectively distribute/split the flows/channel velocities by 1/9 to 1/12. This velocity split allows for improved contact time for the compounds to enter to the pores of a solid support. Thus, the denuder velocities are still significantly high for a thin layer of solid support to function effectively in this multi-channel system, and the solid support must also be designed to function effectively in high velocity systems.

The synthesis of high-performance, multi-porous carbons for high velocity air sampling has become the most effective approach to active sampling tube sampling. Furthermore, the use of an effective 2.0 µm carbon adsorbent, adhered to the side walls of the denuder in a 5.0 µm layer, has shown an effective adsorption/capture of the compounds. Previously published work has provided insight into the benefits of these multi-porous carbons, i.e. synthetic carbons prepared from synthetic polymers, thereby providing for effective desorption of the compounds compared to naturally sourced carbons, such as coal-based or coconut shell-based carbons.

FIG. 3 shows a diagram of velocity vs. HETP illustrating that the incorporation of larger pores at the surface of the particles provides for effective kinetics at high velocity. The y-axis represents 1/efficiency (HETP). The flat slope of the lines with the presence of macropores and mesopores allows the compounds to easily enter the pores of the carbon and transfer to the micropores, where the work is being performed.

The velocity changes as the compounds enter the pore structure of the tested Carboxen-1006 are important for several reasons. The external (interstitial) velocity and the macropore velocity are similar, and therefore the compounds enter the pores at the same velocity. This improves the capacity of the carbon. Also, once the compounds enter the particle, the velocities decrease, therefore allowing for effective adsorption (i.e. condensation) in the 3-dimensional micropore regions.

The use of an effective, high molecular weight adhesive which wraps around the outside of the particles and does not interfere with the adsorbent's pores, where the work is being done, is also an embodiment of the denuder device used in the present invention.

FIG. 4 illustrates the pore structure of the tested multi-porous carbon molecular sieve (Carboxen-1006).

Further, Table 1 below provides data illustrating the improved surface area usages of from multi-porous carbons Supelco (425-850 μm), typically packed in tubes, compared to activated charcoal and several microporous polymer carbons. Carboxen-569 is similar to the Carboxen-1006, Carboxen-1006 being stronger. Carboxen-1006 is not included here due to its particle size at 2.0 μm.

| Adsorbent | breakthrough volume (liters) | Surface area (m2/g) CH2Cl2 | N2 | Surface usage (%) |
|---|---|---|---|---|
| Carbosieve S-III | 66.2 | 697 | 820 | 85 |
| Carboxen-569 | 43.2 | 466 | 485 | 96 |
| Activated charcoal | 39.2 | 526 | 1070 | 49 |
| Carbosieve S-II | 31.5 | 506 | 1060 | 48 |
| Carboxen-564 | 31.5 | 380 | 400 | 95 |
| Purasieve | 5.05 | 364 | 950 | 38 |
| Carboxen-563 | 1.56 | 291 | 510 | 57 |
| Spherocarb | 1.05 | 291 | 880 | 33 |

Thus, with the method according to the present invention the amount of respirable and/or inhalable particles in a fluid flow during a specific time period may be determined, as well as the identity and amount of specific gas phase organic and non-organic components in the fluid flow during the specific time period, in a more accurate way compared to known techniques. Further, a better separation between particles and gas phase component is obtainable, as well as an increased binding of gaseous organic components to the sorbent surfaces.

The previous problem with underestimation of particle concentrations due to evaporation of volatile oil particles from the filter medium will be eliminated by collecting e.g. gas phase oil mist and vapor before the filter, i.e. in the first denuder device 1. Further, the sampling device used in the method according to the present invention is more stable and resists higher loads of fluid flows compared to presently used sampling devices in this technical area. The improved capacity of the first denuder device 1 will minimize the risk of overloading in the sampling device. Further, the back pressure of the samplers will be much less. Another advantage with the method according to the present invention is that it can be performed with a passive fluid flow, i.e. without need of any actively induced fluid flow. The sampler allows sampling at different flow rates as the back pressure is not the limiting factor. In one embodiment a sampling flow between 1-1000 mL per minute can be accomplished during several hours.

While the invention has been described with reference to a number of embodiments, it will be understood by those skilled in the art that various changes may be made and equivalents may be substituted for elements thereof without departing from the scope of the present invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

The invention claimed is:

1. A method for active or passive sampling of particles and gas phase organic and non-organic components in a fluid flow, wherein
   a) a sampling device comprising a first denuder device, a filter device, and a second denuder device, arranged in axial direction in a series in said order, is provided at a measurement spot, wherein the first denuder device and the second denuder device each is hollow and contains surfaces provided with a hydrophobic and/or a hydrophilic sorbent, or said second denuder device contains a packing of hydrophobic and/or hydrophilic sorbent particles,
   b) the fluid flow, which contains gas phase organic components, gas phase non-organic components, and particles, optionally having gaseous organic and/or non-organic components bound thereto, is introduced in the sampling device during a predetermined time period,
   c) gas phase organic and/or non-organic components are bound to the hydrophobic and/or hydrophilic sorbent in the first denuder device, and the particles are allowed to pass through the first denuder device and to enter the filter device,
   d) particles having a diameter exceeding a certain limit value are captured in the filter device, and any gaseous organic and/or non-organic components bound to said captured particles in the filter device are released therefrom,
   e) particles having a diameter which is lower or equal to said limit value, and said any gaseous organic and/or non-organic components released from the particles captured in the filter device are allowed to enter the second denuder device and are bound to the hydrophobic and/or hydrophilic sorbent therein,
   f) gas phase organic components bound in the first denuder device are released from the hydrophobic sorbent therein by thermal desorption, and the particles and the gaseous organic components bound in the second denuder device are released from the hydrophobic sorbent therein by thermal desorption, g) gas phase non-organic components bound in the first denuder device are released from the hydrophobic and/or hydrophilic sorbent therein by chemical extraction, h) the particles and the gaseous organic and/or non-organic components bound in the second denuder device are released from the hydrophobic and/or hydrophilic sorbent by chemical extraction, and i) the identity and amount of particles having a diameter which is lower or equal to said limit value, as well as the identity and amount of gaseous organic and/or non-organic components, is determined for the predetermined time period and the fluid flow rate.

2. The method according to claim 1, wherein one or more different reagents specific for one or more gaseous organic and/or non-organic components and/or particles in the fluid flow are provided on the hydrophobic and/or hydrophilic sorbent in the first denuder device and/or on the hydrophobic and/or hydrophilic sorbent surfaces or particles in the second denuder device, wherein the reagent preferably is gold for the reaction with mercury, one or more primary or secondary amines, preferably dibutylamine (DBA), for the reaction with isocyanates and anhydrides, acidic reagents for the reaction with amines to form ion-pairs, alkaline reagents for the reaction with acids to form ion-pairs, or hydrazines to form hydrazones with aldehydes or ketones.

3. The method according to claim 1, wherein the fluid flow is allowed to pass the sampling device passively without any external force applied for the passage.

4. The method according to claim 1, wherein a pre-selector device, preferably a virtual impactor, is provided between the first denuder device and the filter device or before the first denuder device, wherein a first fraction of predominantly larger particles determined with the basis of a predetermined particle size calibration curve based on a specific particle diameter limit value is captured in the pre-selector device, wherein a second fraction of predominantly smaller particles, which not are captured in the pre-selector device, is allowed to pass through the pre-selector device together with the gas phase organic and/or non-organic components.

5. The method according to claim 1, wherein the fluid flow contains at least one of an oil mist component, an oil vapor component, an industrial waste component, a contaminated water component, an industrial emissions component, an indoor air component, an outdoor air component, an inorganic gas component, a bacteria component, an allergen component, a fungus component, a spore component, a biological compound component, a gaseous organic compound component, a benzene component, a solid air pollutant component, a liquid air pollutant component, an asbestos component, a dust component, a metal component, a volatile organic compound (VOC) component, a chemical warfare agent component, an anesthetic agent component, an isocyanate component, an aromatic isocyanate component, an aliphatic iso-cyanate component, a butylisocyanate (BIC) component, a propylisocyanate (PIC) component, an iso-propylisocyanate (i-PIC) component, an ethylisocyanate (EIC) component, a methylisocyanate (MIC) component, an isocyanic acid (ICA) component, an aminoisocyanate component, an isothiocyanates component, an anhydride component, an ammonia ($NH_3$) component, an aliphatic amine component, an aromatic amines component, a dimethylamine (DMA) n-butylamine (n-BA) component, a methylene dianiline (MDA) component, a p-phenylene diamine (PPD) component, a 2,4-toluene diamine component, a 2,6-toluene diamine component, an alfa-naphtylamine trimethylamine component, a beta-naphtylamine trimethylamine component, a diisocyanates component, a cyclohexyl diisocyanate (CHDI) component, a hexamethylene diisocyanate (HDI) component, a dicyclohexyl metan diisocyanate (HMDI) component, an IEM component, an isophorone diisocyanate (IPDI) component, a 4,4'-methylene diphenylisocyanate (MDI) component, a naphtyldiisocyanate (NDI) component, a paraphenylene diisocyanate (PPDI) component, a 2,4-toluene diisocyanate component, a 2,6-toluene diisocyanate component, a trimethylhexamethylene diisocyanate (TMDI) component, a trimethyl xylene diisocyanate (TMXDI) component, a xylenediisocyanate (XDI) component, a hydrazine component, a monomethylhydrazine (MMH)component, a ($N_2H_4$) component, a 1,1 dimethylhydrazine (DMH) component, a hydrides component, an arsine ($AsH_3$) component, a diborane ($B_2H_6$) component, a disilane ($Si_2H_6$) component, a germane ($GeH_4$) component, a hydrogen selenide ($H_2Se$) component, a phosphine ($PH_3$) component, a silane ($SiH_4$) component, a stibine ($SbH_3$) component, a tert-butylarsine (TBA) component, a tert-butylphosphine (TBP) component, a hydrogen cyanide (HCN) component, a hydrogen sulfide ($H_2S$) component, a mineral acid component, a hydrogen bromide (HBr) component, a hydrogen chloride (HCl) component, a hydrogen fluoride (HF) component, a hydrogen Iodide (HI) component, a nitric acid ($HNO_3$) component, a sulfuric acid ($H_2SO_4$) component, an oxidizer component, a bromine ($Br_2$) component, a chlorine ($Cl_2$) II component, a chlorine dioxide ($ClO_2$) component, a hydrogen peroxide ($H_2O_2$) component, a nitrogen dioxide ($NO_2$) component, an ozone ($O_3$) component, a phosgene ($COCl_2$) component, and a sulfur dioxide ($SO_2$) component.

6. The method according to claim 1, wherein the hydrophobic and/or hydrophilic sorbents in the first denuder device are provided on the inner and/or outer surfaces of several channels extending in the axial direction of the first denuder device or on one of or both of the surfaces of elements extending in the axial direction of the first denuder device, and wherein the hydrophobic and/or hydrophilic sorbents in the second denuder device are provided on the inner and/or outer surfaces of several channels extending in the axial direction of the second denuder device, or on one of or both of the surfaces of elements extending in the axial direction of the second denuder device, or on the surfaces of packed hydrophobic and/or hydrophilic sorbent particles in the second denuder device.

7. The method according to claim 5, wherein said channels have a quadratic, circular, or hexagonal cross-section, and wherein said elements have a zigzag or spiral cross-section form.

8. The method according to claim 1, wherein each hydrophobic and/or hydrophilic sorbent has an acidic or alkaline pH value.

9. The method according to claim 1, wherein the sorbents on the surfaces in the first denuder device, in the second denuder device, and the sorbent particles in the second denuder are carbon particles, preferably synthetic carbon molecular sieves and/or graphitized, or preferably comprising graphene, having a diameter in the nanometer —millimeter range, and/or said sorbent particles are made of plastic polymers, or silica having a surface layer of polymers or organic molecules.

10. The method according to claim 1, wherein the identity and amount of particles, gas phase organic and non-organic components, and gaseous organic and non-organic components released from and emitting the sampling device are determined by use of ICP-MS (Inductively Couple Plasma-Mass Spectroscopy) or atomic absorption spectrometry, GC-FID (Gas Chromatography-Flame Ionization Detection), GC-MS (Gas Chromatography-Mass Spectroscopy), LC-MS (Liquid Chromatography-Mass Spectrometry), bio-analytical techniques, preferably immunological methods, for determining bacteria, fungi or other bio-molecules, electro-chemical determination, preferably using electrophoresis or ion-exchange methodology, and weighing before and after the passage of the sampling device.

11. The method according to claim 1, wherein the limit value of the particle size diameter used in the filter device is 4 μm in the case of respirable particles, and 10 μm in the case of inhalable particles, wherein the pre-selector device is a virtual impactor, and wherein the separation between the fraction of predominantly larger and smaller particles in the virtual impactor is based on a d50 particle cut-off value of 2-100, preferably 4 μm.

12. The method according to claim 11, wherein the first particle fraction separated from the fluid flow in the virtual impactor is withdrawn from the sampling device via an outlet and is analyzed in view of identity and amount.

13. The method according to claim 1, wherein the thermal desorption is performed at a temperature level of at most 230° C., preferably at most 190° C.

14. The method according to claim 1, wherein the sampling device is regenerated by heating and purging it from said gaseous organic and/or non-organic components and particles previously captured in the first denuder device and in the second denuder device.

15. The method according to claim 1, wherein the filter device is a high-efficiency particulate arresting (HEPA) filter.

\* \* \* \* \*